United States Patent [19]
Harke et al.

[11] Patent Number: 5,684,598
[45] Date of Patent: Nov. 4, 1997

[54] PROCESS FOR MONITORING A MOVING YARN SHEET AND APPARATUS FOR THE EXECUTION OF THIS PROCESS

[75] Inventors: Peter Harke, Selfkant; Hans Willi Louis, Heinsberg; Wolfgang Worbs, Gangelt, all of Germany

[73] Assignee: Akzo Nobel NV, Arnhem, Netherlands

[21] Appl. No.: 586,122

[22] Filed: Jan. 16, 1996

[30] Foreign Application Priority Data

Jun. 24, 1995 [DE] Germany ............... 195 23 055.8
Jul. 21, 1995 [DE] Germany ............... 195 26 646.3

[51] Int. Cl.$^6$ ............................................. G01N 21/89
[52] U.S. Cl. ............................... 356/430; 356/238
[58] Field of Search ............................... 356/238, 429, 356/430; 250/559.45, 559.46

[56] References Cited

U.S. PATENT DOCUMENTS

| | | | |
|---|---|---|---|
| 3,717,771 | 2/1973 | Abilock et al. | 250/219 |
| 3,786,265 | 1/1974 | Abilock et al. | 250/219 |
| 4,952,062 | 8/1990 | Bear, III et al. | 356/430 |
| 5,313,692 | 5/1994 | Mizucchi et al. | 356/430 |
| 5,426,509 | 6/1995 | Peplinski | 356/430 |

FOREIGN PATENT DOCUMENTS

4236413C1 10/1992 Germany .............. G01B 11/10

OTHER PUBLICATIONS

Derwent Abstract Info. 1995 for German Patent No. DE4236413C1.

Primary Examiner—Frank G. Font
Assistant Examiner—Zandra V. Smith
Attorney, Agent, or Firm—Joseph M. Noto; Louis A. Morris

[57] ABSTRACT

Process for monitoring a moving yarn sheet by means of a light beam, photodetectors and an electronic analyzer, whereby the yarn sheet is guided via thread guide rods before and after the monitoring site and the shadowing of the light beam caused by an increase in thread thickness is directed perpendicularly to the direction of travel of the yarn sheet for detection by photodetectors, and evaluated and recorded by the electronic analyzer, characterized in that the intensity of a single light beam is detected by at least two photodetectors arranged in series in the direction of travel of the yarn sheet and in that the evaluation by the electronic analyzer is such that a recording only takes place when the shadowing is detected by one or more of said photodetectors following in the direction of travel of the yarn sheet with a time delay corresponding to the running speed of the yarn sheet is disclosed. It is preferred to employ at least four photodetectors of which at least two are situated in series in the direction of travel of the yarn sheet and at least two are arranged one above the other such that at least one photodetector is positioned below the yarn sheet plane and at least one photodetector is positioned above the yarn sheet plane.

24 Claims, 9 Drawing Sheets

Fig.15

PROCESS FOR MONITORING A MOVING YARN SHEET AND APPARATUS FOR THE EXECUTION OF THIS PROCESS

CROSS REFERENCE TO RELATED APPLICATIONS

This application claims the benefit of the filing dates of prior German Patent Application Nos. 195 23 055.8, filed Jun. 24, 1995 and 195 26 646.3, filed Jul. 21, 1995, which are each incorporated herein by reference in their entirety.

BACKGROUND OF THE INVENTION

1. Field of the Invention

The present invention relates to a process for monitoring a moving yarn sheet whereby the yarn sheet is guided by means of thread guide rods before and after the monitoring site, a light beam is sent out perpendicular to the direction of travel of the yarn sheet and parallel to the yarn sheet plane to photodetectors, and the signals of the photodetectors are evaluated and recorded by means of an electronic analyzer, as well as an apparatus to implement this process.

2. Description of the Related Art

U.S. Pat. No. 3,717,771 relates to a process which is characterized by a light beam focused on two sequential positions perpendicular to the direction of travel of the yarn sheet, through the yarn sheet, into a photodetector beyond the yarn sheet. To avoid occurrences of thread plucks or thread jumps, which cast similar shadows into the light beam and onto the photodetector thus causing a signal change, being received and recorded as thread thickness errors (lint, knots, etc.), a second photodetector is connected into which a corresponding second light beam is focused if the first monitoring position has perceived a shadow. If, after a time span corresponding to the time span up to which the shadowing of the second light beam should take place and which can be calculated from the distance between both photodetectors and the running speed of the yarn sheet, a shadowing is also recorded by the second photodetector, a recorded signal is then relayed via an electronic analyzer. This recorded signal is employed for counting thread thickness errors of the yarn sheet or as a yarn sheet stop signal so that the thread error can be corrected.

Due to the constant desire to increase running speeds of the yarn sheets under discussion an increase in thread plucks and thread jumps can be observed. If such thread plucks or thread jumps occur in a time span corresponding to the time span between the measurement at the first and the second photodetector, such thread plucks or thread jumps will also cause a recorded signal. It was at this point ascertained that because of thread plucks and thread jumps the known procedure will give a number of thread thickness errors which is up to 100% higher than the number of thread thickness errors actually existing. Additionally the arrangement of two monitoring points, with the thread guide rods before and after the monitoring point, necessary for measuring, requires correspondingly sufficient space. Therefore, apparatuses in which running yarn sheets are to be treated (warping frame, sizing machine, wet spinning frame, etc.) must have an extended construction. However, an accurate recording of thickness errors will not take place.

DE-C-42 36 413 proposes that thread plucks and thread jumps are to be avoided by guiding the yarn sheet in the area of the monitoring point by means of a guide bar and by the fact that the monitoring of the yarn sheet takes place from the side opposite the guide bar. Also it should be pointed out here that only by the series connection of two of the described apparatuses and the coupled analyses of both apparatuses is the detection reliability improved. Apart from furnishing the required space for the series connection of the two apparatuses, the guide rod furnishes simultaneously an additional strain on the yarn sheet, so that multiple occurrences of the described apparatus are undesirable. The danger also exists that lints are deformed by the guide rod, so that they can no longer be recognized.

SUMMARY OF THE INVENTION

One aspect of the present invention is to improve the recording precision of thread thickness errors of a moving yarn sheet in the process of the type initially described.

This aspect is met by the process of the present invention by determining the intensity of a single light beam by at least two photodetectors which are positioned one after another in the direction of travel of the yarn sheet and by the fact that the analysis is carried out by means of the electronic analyzer in such a way that recording only occurs when one or more photodetectors following in the direction of travel of the yarn sheet detect the shadow with a time delay corresponding to the running speed of the yarn sheet.

Thus in this manner, the technical expenditure will be reduced because the light source and the devices necessary for the homogenization of the light are only necessary one time. Both the photodetectors are generally arranged directly adjacent. Thread plucks or thread jumps occurring in such short time intervals that two consecutive thread plucks or thread jumps are recorded as thread thickness errors occur rarely, so that the recording precision of the apparatus of the invention, which requires less expenditure per se, is significantly improved.

It has been shown to be advantageous if the light beam is widened before incidence with the yarn sheet. The spreading of the light beam can be effected in a simple way with the corresponding optical lens.

The process of the invention succeeds particularly well if the light beam is widened to a maximal 30 mm, and if the breadth of the light beam is focused beyond the yarn sheet in such a way that it illuminates all photodetectors assigned to it. Preferably the light beam is sent through the yarn sheet at a maximal 10 mm breadth and focused behind the yarn sheet so that at least the entire surface area of the assigned photodetectors is covered. To make sure that no erroneous measurements occur, for instance through vibrations, the focused width and height of the light beam is as a rule defined so that the width and height of the light beam is set larger than is necessary for a complete illumination of the assigned photodetectors. If the photodetectors are known to have a total surface area of 3 mm×3 mm, for example, then it is recommended to focus the light beam to 5 mm by 5 mm.

In this case it has proven especially useful if the light beam is directed into two photodetectors included in a double photodetector unit. Double photodetector units are available commercially and are characterized by particularly small dimensions. The illumination surface of both photodetectors of a double photodetector unit, where both photodetectors are positioned side by side, can be, for instance, 3 mm by 3 mm in size.

This and other aspects of the present invention will become apparent upon a review of the following detailed description and the claims appended thereto.

DETAILED DESCRIPTION OF PREFERRED EMBODIMENTS

The process of the present invention is characterized by particular measurement accuracy and simplicity, as shown by the fact that the amplified signals of two photodetectors in series, struck by a single light beam, are relayed to a differential amplifier and the electronic analyzer will only transmit a signal for recording when the differential signal exceeds a predetermined threshold. In case of a thread pluck or a thread jump both photodetectors will receive the same signal simultaneously, so that both signals are canceled out in the differential amplifier, and as a result no further signal is emitted by the differential amplifier. In case of a lint or some other thread thickness error the signal of the second photodetector is relayed to the differential amplifier with a time delay in relation to the signal of the first photodetector, so that the differential amplifier then emits a signal.

It can be an advantage if the process of the invention is repeated in the direction of travel of the yarn sheet. Repetition of the process, however, requires no interval between both monitoring points as large as required for the execution of the process that is known from U.S. Pat. No. 3,717,771, which is incorporated herein by reference in its entirety. This represents one simple possibility for a control mechanism.

The objective set for the invention and met by the initially described process, where at least one light beam is employed, is likewise met by using one or more light beams and at least four photodetectors for monitoring, of which at least two are in series in the direction of travel of the yarn sheet and at least two are arranged one above the other, so that at least one photodetector is below and at least one photodetector is above the plane of the yarn sheet.

By means of the photodetectors arranged one above the other, a simple determination is hereby made whether a thread pluck or thread jump has occurred, while the series arranged photodetectors will determine the size of the shadow. As a result it is possible to eliminate most of the signals attributable to thread plucks or thread jumps and to determine as well the thickness when a thickness error occurs. The necessary comparisons will be performed by the connected electronic analyzer.

Practically all types of light which can be collimated are suited for the light beams. Laser beams are particularly effective.

Preferably, half of all photodetectors are arranged above the plane of the yarn sheet and the other half of all photodetectors are arranged below the plane of the yarn sheet. In the case of four photodetectors, two photodetectors are arranged above the yarn sheet plane and two below the yarn sheet plane, whereby the two photodetectors above and below are positioned one after another. A corresponding arrangement applies when six, eight or more photodetectors are installed, in which case an even number of photodetectors is required for this embodiment.

It has been found to be most effective if each upper photodetector is arranged adjacent to a respective lower photodetector and/or if photodetectors in series are arranged adjacently. This arrangement enables precise detection of small thread thickness errors so that no significant falsifications due to thread plucks or thread jumps result.

This embodiment for monitoring of the yarn sheets requires minimal space while providing higher precision in monitoring. The precision of the monitoring is improved as more photodetectors are employed.

The process of the invention is characterized in particular in that the electronic analyzer is able to differentiate a lint signal, which is formed by summing up the signals sent by the photodetectors positioned one above the other and by calculating the difference between the sums detected by two photodetector pairs positioned one after another, and a thread jump signal, which is created by summing the signals sent by photodetectors positioned one after another and by calculating the difference of the sums detected by the two photodetector pairs positioned one above the other, and in that a lint is recorded when the difference of the lint signal minus the attenuated thread jump signal exceeds a predetermined lower threshold value.

Reworking or possibly eliminating lints or other thread thickness errors from a certain size on in a yarn sheet can easily be carried out when using the process of the invention. When a lint signal exceeds a predetermined upper threshold value and a lint has simultaneously been recorded the electronic analyzer can send a stop signal. By means of this stop signal the moving sheet can be stopped via means commonly known to one skilled in the art.

Less pronounced thread thickness errors can also be detected easily. Here, the process of the invention is especially suitable if the electronic analyzer determines the lint size via the strength of the lint signal when a lint is recorded.

Embodiments with at least four photodectors can also employ multiple light beams instead of a single light beam. However, the process of the invention using at least four photodetectors can be designed to save significant space if all photodetectors are subject to illumination by one light beam.

To carry out the process of the invention in the case where the light beam is widened before incidence with the yarn sheet, the light beam should be focused after passing through the yarn sheet so that the light beam illuminates all photodetectors allocated to it. A light beam width of 10 mm maximum and a focusing width of 6 mm maximum has proven especially satisfactory.

The process of the invention succeeds particularly well when carried out using double photodetector units, especially four-quadrant or multisegment photodetector units.

An apparatus suited for carrying out the process of the invention to monitor a moving yarn sheet with at least one light source and photodetectors is characterized in that the apparatus features at least two photodetectors which are positioned one after another in the direction of travel of the yarn sheet and which are illuminated by a single light beam.

An apparatus especially suited for carrying out the process of the invention to monitor a moving yarn sheet with at least one light source and photodetectors is characterized by the fact that the apparatus features at least four photodetectors of which at least two photodetectors are positioned one after another in the direction of travel of the yarn sheet and at least two photodetectors are positioned one above the other.

A preferred embodiment of the apparatus of the invention is characterized by the fact that all photodetectors are positioned so that pairs positioned one above the other are formed and that all pairs are positioned one after another.

It is favorable if 50% of all photodetectors are positioned above and 50% below the yarn sheet plane.

BRIEF DESCRIPTION OF THE DRAWINGS

The apparatus of the invention is explained more fully in the following in detail with reference to the following figures, whereby

FIG. 3b shows the signal emitted by a differential amplifier after reception of the signals depicted in FIG. 3a;

FIG. 4b shows the signal emitted by a differential amplifier when receiving the signals depicted in FIG. 4a;

FIGS. 9 a–g show the waveforms of the analyzer of FIG. 5 when a lint passes through;

FIGS. 10 a–g show the waveforms of the analyzer of FIG. 5 in the case of thread jumps of FIG. 3;

FIGS. 11 a–g show the waveforms of the analyzer of FIG. 5 for thread jumps of FIG. 4;

Figure 1:
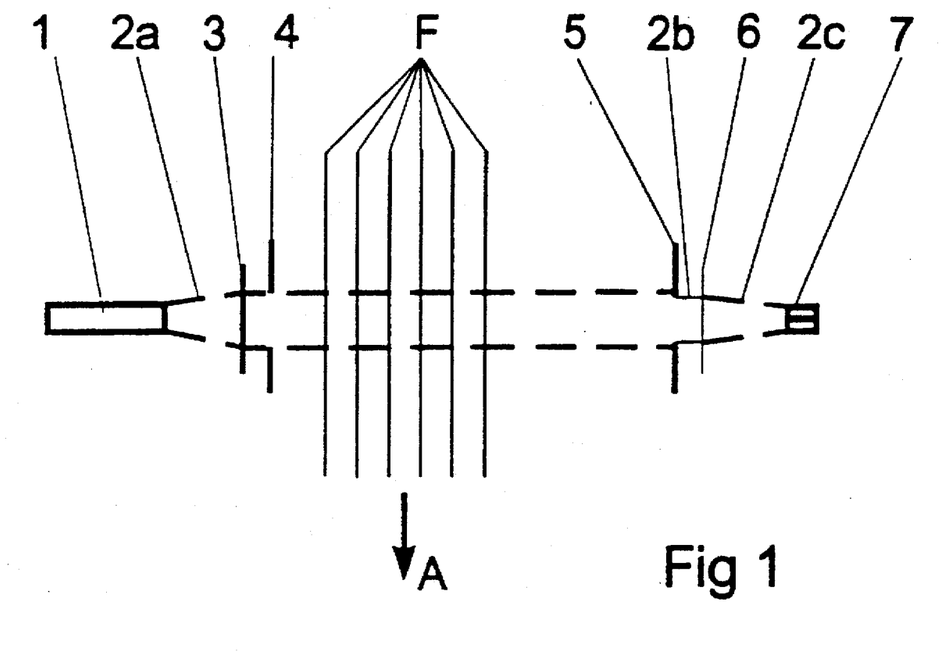
FIG. 1 shows schematically an apparatus suited for the execution of the process of the invention.

In FIG. 1 the light source is referred to as 1. Practically all types of light which can be collimated are suited for the light beams. Laser beams are found to be most effective. The diverging light beam in 2a is collimated by an optical device, for instance a lens 3, and an aperture 4 adjusts the light beam to the desired width. The light beam, thus homogenized and adjusted in width (and height) is perpendicularly focused on the threads F of a yarn sheet and strikes beyond the yarn sheet another aperture 5, which diaphragms the outer edge of the light beam. The light beam 2b, whose width is reduced, is focused via another optical lens 6. The focused light beam 2c strikes double photodetector unit 7.

Figure 2:
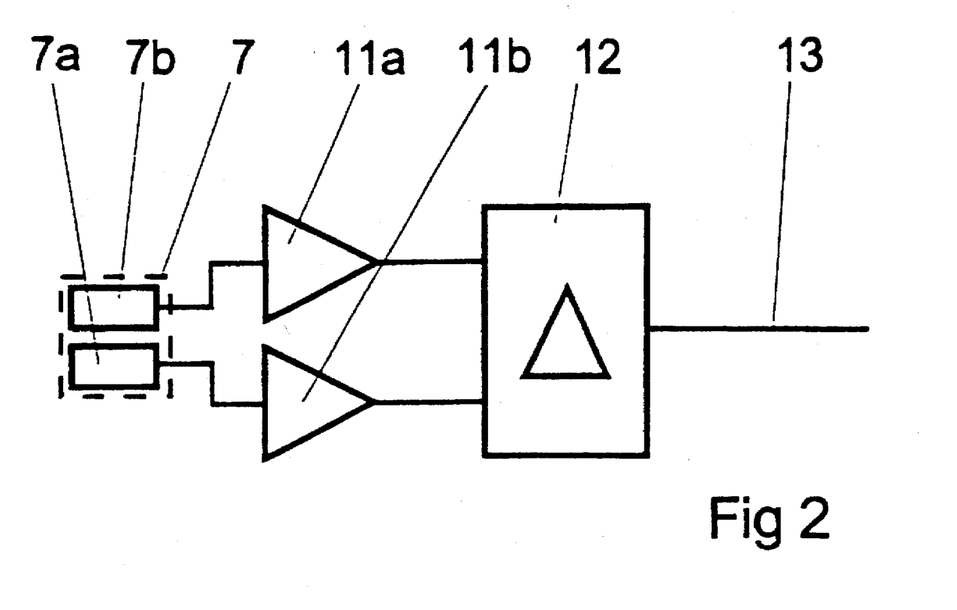
FIG. 2 shows schematically an electronic analyzer suited for the execution of the process of the invention.

As depicted in FIG. 2, the double photodetector 7 consists of two photodetectors 7a and 7b relaying their signals to amplifiers 11a and 11b, as illustrated here in an especially preferred embodiment of the process of the invention. The amplified signals are relayed to a differential amplifier 12 which in turn transmits the analyzed signal 13 if one does exist. This signal 13 can, for instance, be relayed to a counting device (not illustrated). Signal 13 can also be used to shut down the apparatus which moves the yarn sheet so that the operating personnel can eliminate as far as possible the detected error.

Figure 3:
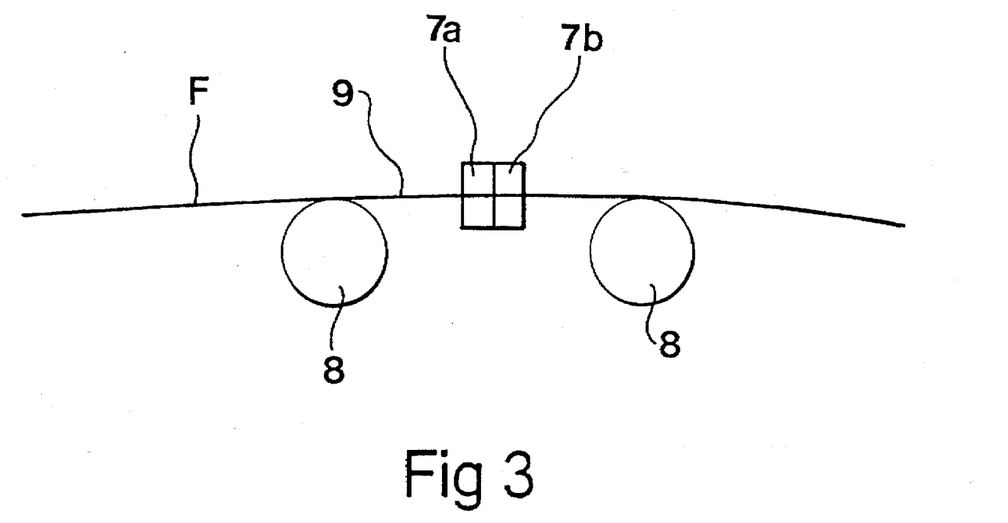
FIG. 3 shows a yarn sheet with a thread lint.
Figure 3A:
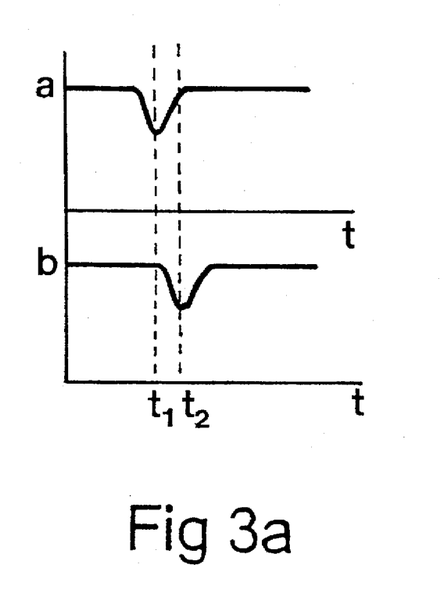
FIG. 3a shows the signals emitted by the photodetectors in the case of a thread lint.
Figure 3B:
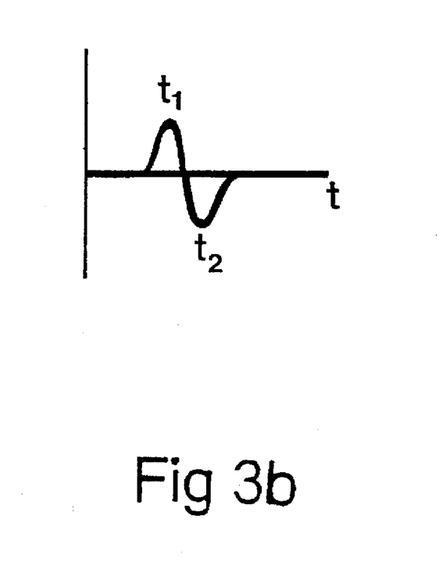

FIG. 3 depicts a side view of the yarn sheet F, whereby the line of sight is directed from the light source onto the yarn sheet. Two photodetectors 7a and 7b are visible behind the yarn sheet. For clarity, the light beam, aperture 5, and lens 6 are omitted. The yarn sheet is guided over two thread guide rods 8, so that the yarn sheet is positioned horizontally at the monitoring site. It is assumed that the yarn sheet F in FIG. 3 moves from left to right, whereby one of the threads of yarn sheet F contains a lint 9. When lint 9 enters the area encompassed by the light beam and first projects a shadow upon photodetector 7a at time point t1 and then projects a shadow upon photodetector 7b at time point t2, it gives rise to the signal emitted by photodetector 7a depicted in "a" of FIG. 3a and the signal emitted by photodetector 7b depicted in "b" of FIG. 3a. Both signals are plotted over a time axis, whereby both time points t1 and t2 are depicted as broken lines. When these signals are relayed to a differential amplifier and the differential amplifier is connected such that it subtracts signal "b" from signal "a", the differential amplifier emits a signal as depicted in FIG. 3b.

Figure 4:
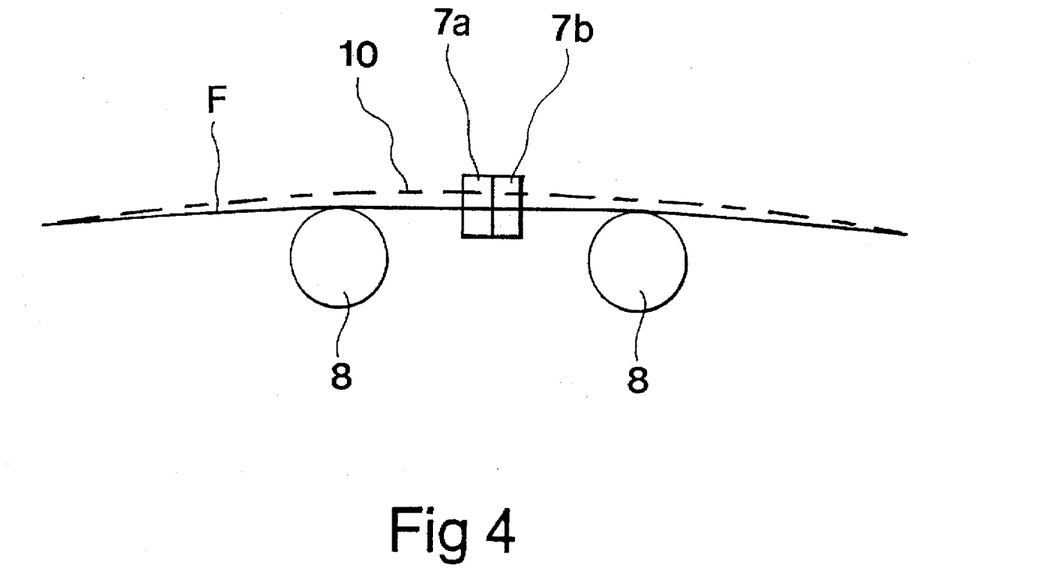
FIG. 4 shows a yarn sheet with a thread jump.
Figure 4A:
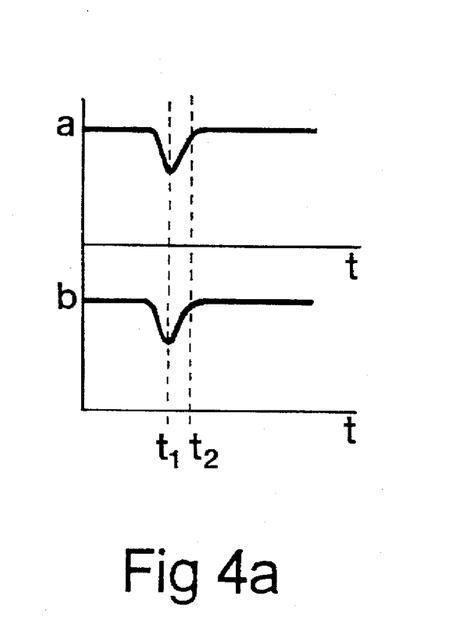
FIG. 4a shows the signals emitted by the photodetectors in case of a thread jump.
Figure 4B:
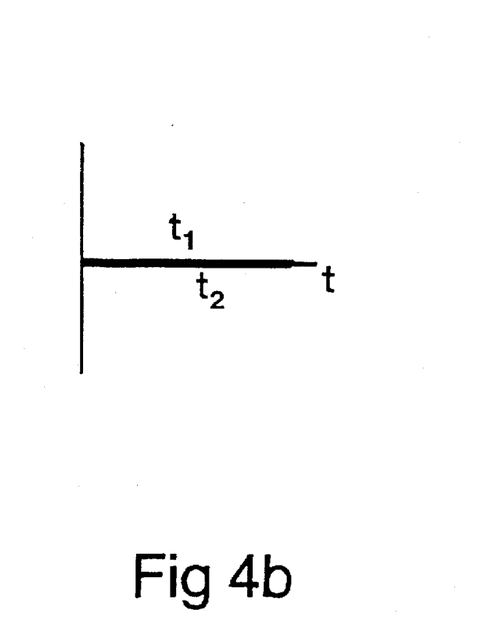

FIG. 4 depicts a side view of yarn sheet F whereby the line of sight is directed as previously from the light source toward the yarn sheet. Behind the yarn sheet only the two photodetectors 7a and 7b are visible. A thread jump at time point t1, as depicted by thread 10 of yarn sheet F, results in a shadow projecting simultaneously upon both photodetectors 7a and 7b. At time point t2, where the thread which had undergone a thread jump again enters the plane of the yarn sheet F, no shadow is projected upon photodetectors 7a and 7b. This results in waveforms for the two photodetectors as depicted in "a" of FIG. 4a for the signal of photodetector 7a and in "b" of FIG. 4a for the signal of photodetector 7b. Since the thread jump is detected simultaneously by both photodetectors, the identical waveform is emitted by a and b in case of a thread jump. As a result, the differential amplifier relays no signal, as is depicted in the waveform of FIG. 4b. Consequently it is assured that a thread jump is not recorded as a thread error, that is to say, the apparatus for moving the yarn sheet is not stopped.

The following explanations are described in terms of a four-quadrant photodetector since the advantages can be explained more simply hereby. However, these explanations demonstrate that the significance of the monitoring results can be improved by increasing the number of photodetectors. During the execution of the process of the invention it became evident that as a rule two- or four-quadrant photodetectors are adequate for obtaining sufficiently good results. In special cases, for instance in the case of very frequent thread jumps, or if the wish arises to detect particularly small lints it is recommended to increase the number of photocells and to employ multisegment photocells. In reference to FIG. 1, one should assume that a four-quadrant photodetector 7 is employed in the following description instead of the double photodetector as depicted in FIG. 1.

Figure 5:
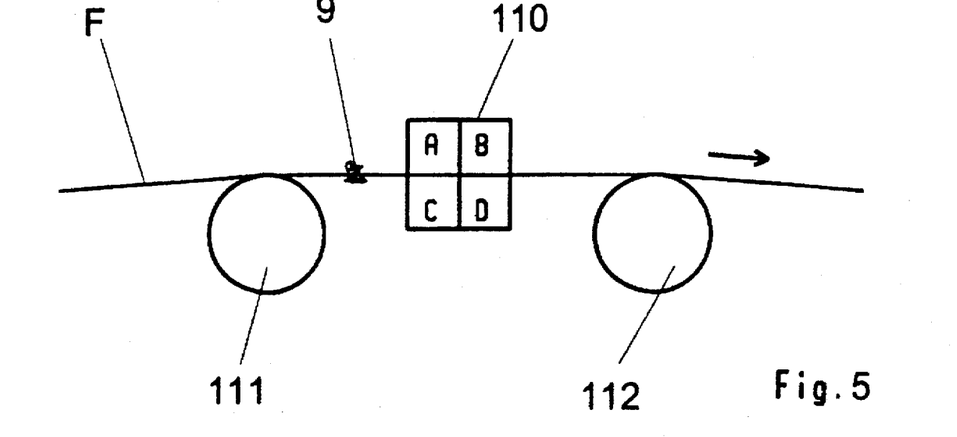
FIG. 5 shows schematically a view of the photodetector perpendicular to the yarn sheet.

As depicted in FIG. 5, the yarn sheet moves past the four-quadrant photodetector 110 such that the plane of the yarn sheet runs parallel to the contact edge between quadrants A and C and between quadrants B and D respectively of the four-quadrant photodetector 110. For precise guiding of the yarn sheet, thread guide rods 111 and 112, not depicted in FIG. 1, are positioned before and after, respectively, the four-quadrant photodetector. According to the figure, quadrants A and B are positioned above the yarn sheet plane adjacently in the direction of travel of the yarn sheet, while quadrants C and D are positioned below the yarn sheet plane, also adjacently in the direction of travel of the yarn sheet. Quadrant A is also adjacent to quadrant C and quadrant B is adjacent to quadrant D.

Figure 6:
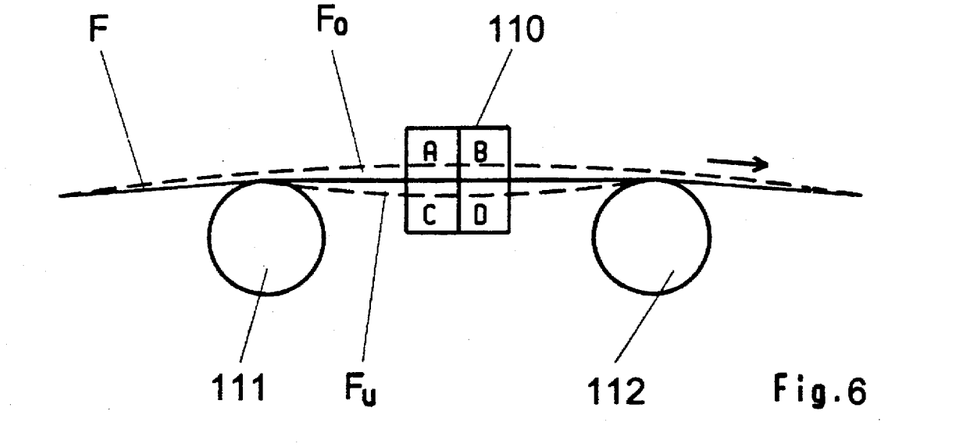
FIG. 6 shows a view of FIG. 2 with thread jumps.
Figure 7:
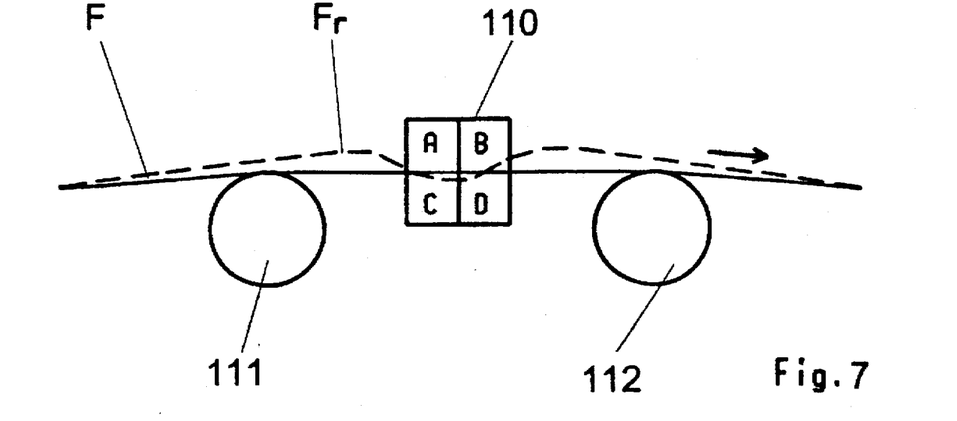
FIG. 7 shows another view of FIG. 2 with another thread jump.

In FIGS. 5 through 7 one proceeds on the assumption that the light beam is focused by aperture 5 and lens 6 such that its external contour corresponds to the external contour of the four-quadrant photodetector 110 so that the external contour of the four-quadrant photodetector 110 also represents the external contour of the light beam. For clarity, the light beam in the area of the yarn sheet, which according to FIG. 1 has a larger cross-section, has not been depicted.

FIG. 6 expands on the situation depicted in FIG. 5 such that the effect of a thread jump, as it appears in the ideal case, is illustrated. Hereby the maximum upward deflection of one or more threads is described as Fo and the maximum downward deflection as Fu.

FIG. 7 depicts another thread jump which appears more frequently in reality than the thread jump depicted in FIG. 5. In the following description such a thread jump is referred to as a real thread jump, Fr.

Figure 8:
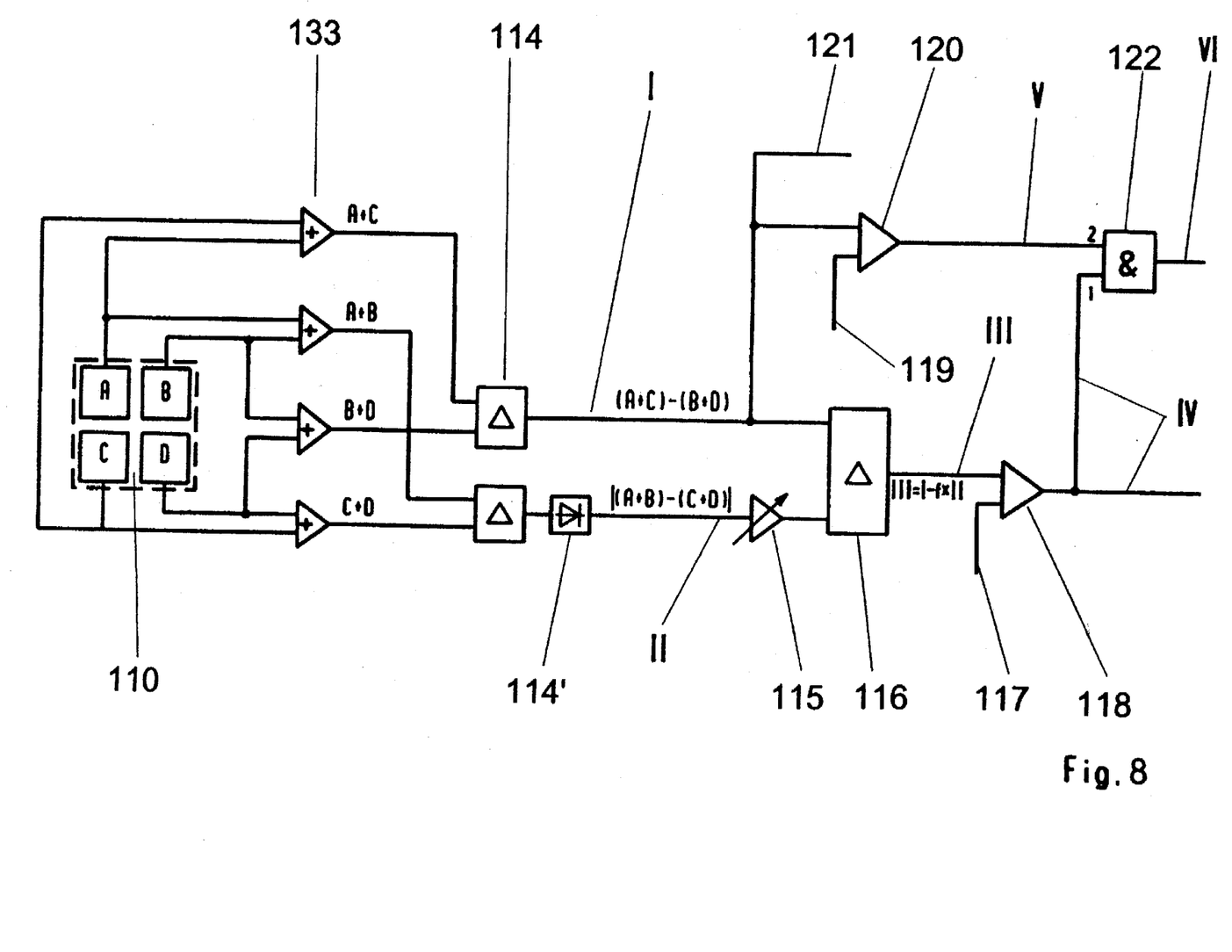
FIG. 8 shows an electronic analyzer suited for the execution of the process of the invention.

FIG. 8 depicts the circuitry of an electronic analyzer suited for the execution of the process of the invention. Initially the signal outputs of the four-quadrant photodetector 110 are relayed to a summing switch 133, where the sums of the quadrants which are adjacent to each other, A+B, C+D, A+C and B+D, are formed. The differences (A+C)–(B+D) and (A+B)–(C+D) respectively are generated by differential switch 114 whereby the difference (A+C)–(B+D) will cause a signal output I, which in the following is called lint signal I, and the difference (A+B)–(C+D) is first rectified by rectifier 114' and then results in a signal output II, which in the following is called thread jump signal II. This thread jump signal II is relayed via an attenuator 115 since a thread jump covers in each quadrant a larger surface area than for instance a smaller lint, whereby the attenuation is carried out by factor f, where 0<f<1. The attenuated thread jump signal II is then subtracted from the lint signal I via a differential switch 116 and leads to an output signal III=I–f II. This output signal III is compared to a predetermined lower threshold value 117 in a threshold switch 118, whereby exceeding the lower threshold value will provoke an output signal IV which is tantamount to the indication "presence of a lint". A counter, which is connected to this output signal IV (not illustrated), will detect the number of lints.

At the same time the lint signal I is compared to an upper threshold value 119 in a threshold switch 120. Exceeding the upper threshold value will emit an output signal V which will emit an output signal VI when an output signal IV is present at the same time. Output signal VI can be employed to stop a moving yard sheet. Output signal VI is emitted when output signal IV and output signal V are fed into an AND element 122. By predetermining the upper threshold value 119, one can determine the minimum lint size that will cause stoppage of the yarn sheet.

Lint signal I can also be employed as an output signal to determine the lint size whereby from this point on each lint can be recorded with its corresponding size via an appropriate evaluation. Here, an appropriate circuit can ensure that the determination of the lint size only takes place when the output signal IV gives the indication "presence of a lint".

Figure 9A:
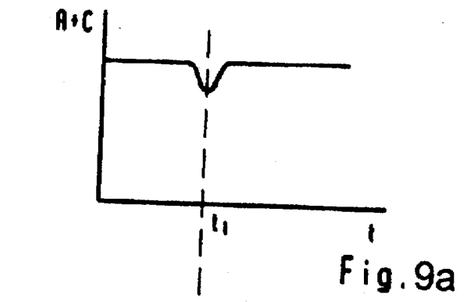
Figure 9B:
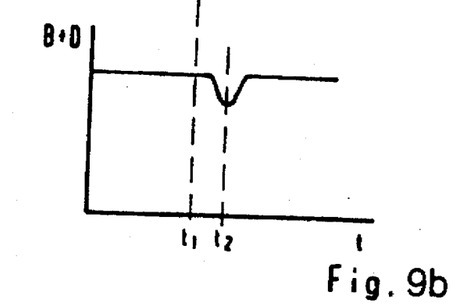
Figure 9C:
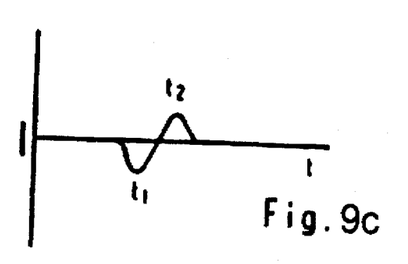

FIGS. 9a through 9g depict the waveforms of the analyzer of FIG. 8 when a lint passes through. FIG. 9a depicts hereby the time sequence of the composite signal A+C and FIG. 9b depicts the time sequence of the composite signal B+D. By forming the difference between the two composite signals, lint signal I is created, the time sequence of which is illustrated in FIG. 9c.

Figure 9D:
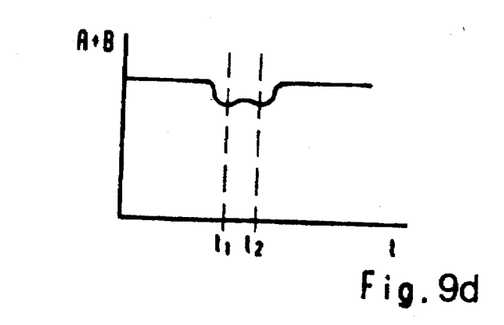
Figure 9E:
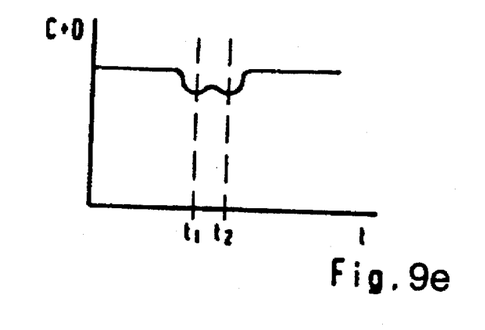
Figure 9F:
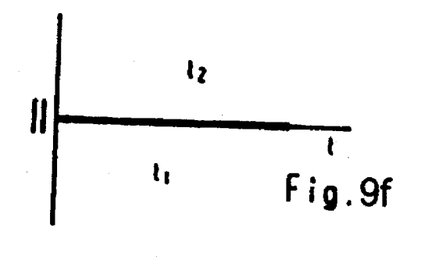

FIG. 9d depicts the time sequence of composite signal A+B and FIG. 9e depicts the time sequence of composite signal C+D. As previously explained, thread jump signal II represents the difference between these two composite signals. FIG. 9f depicts the time sequence of thread jump signal II.

Figure 9G:
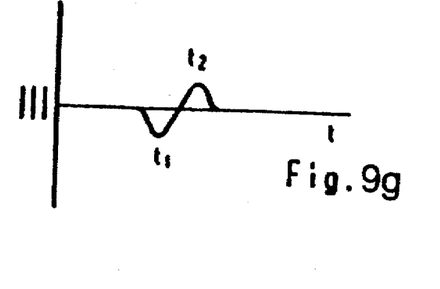

The differential signal which is obtained by subtracting the thread jump signal from the lint signal and which is referred to in the above description as output signal III is described in its time sequence in FIG. 9g.

The illustrated time sequences are based on the assumption that a lint is formed symmetrically and therefore extends upward and downward equidistantly from the thread. In case of an asymmetrical lint, the time sequence depicted in FIG. 9f will be a certain distance from the zero line. This distance will hardly affect the time sequence of output signal III due to the attenuation provided, so that a signal for evaluation can also be obtained for asymmetrical lints.

As previously pointed out and as demonstrated by means of the time sequences shown, the presence of a lint can be clearly recognized (FIG. 9g) by means of the present circuit. The size of the lint can be determined by the amplitude of the time sequence of the lint signal (FIG. 9c).

Figure 10A:
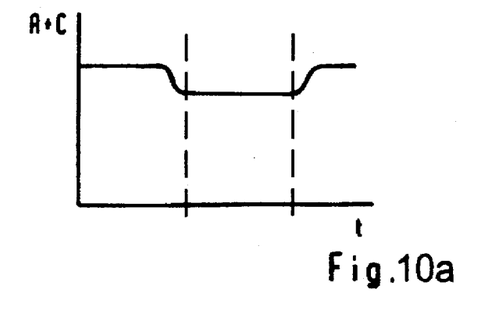
Figure 10B:
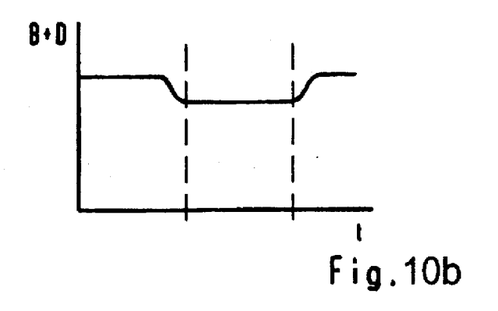
Figure 10C:
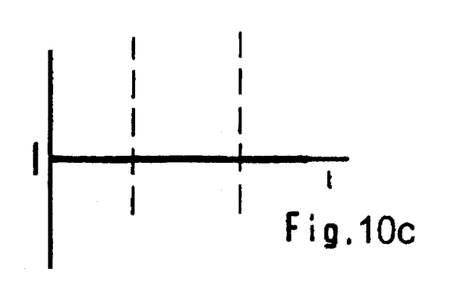
Figure 10D:
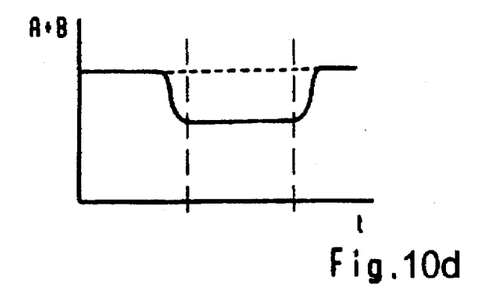
Figure 10E:
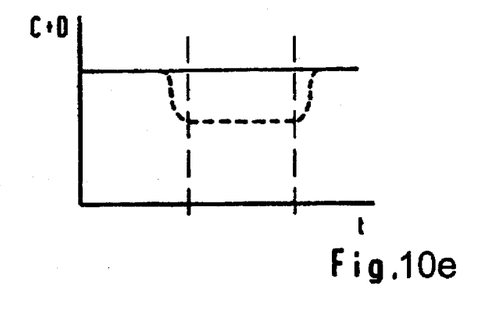
Figure 10F:
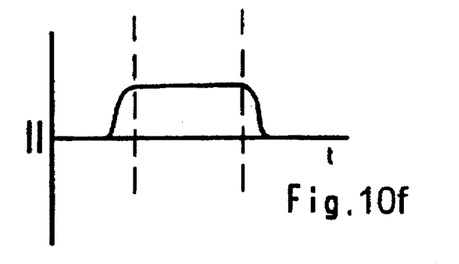
Figure 10G:
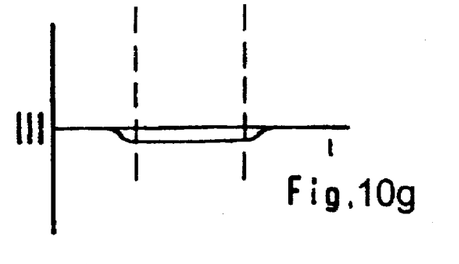

According to FIGS. 10a through 10g, the waveforms of the analyzer are demonstrated in relation to FIG. 8 and in the presence of thread jumps as presented in FIG. 6. Here correspondingly, the time sequences are shown of composite signal A+C in FIG. 10a, of composite signal B+D in FIG. 10b, of the lint signal in FIG. 10c, of the composite signal A+B in FIG. 10d, of the composite signal C+D in FIG. 10e, of the thread jump signal in FIG. 10f and of the output signal III in FIG. 10g. FIGS. 10d and 10e illustrate the time sequence for a thread jump upwards by a solid line and a thread jump downwards by a broken line. FIG. 10g makes it clear that the output signal III does not exhibit positive values and therefore, when compared to a lower threshold value 117, cannot transmit a signal IV, so that this type of thread jump cannot lead to a lint indication.

FIGS. 11a through g depict time sequences of thread jumps as demonstrated in FIG. 7 which are referred to as real thread jumps. Accordingly, the time sequence of the composite signal A+C is again depicted in FIG. 11a, of the composite signal B+D in FIG. 11b, of the lint signal in FIG. 11c, of the composite signal A+B in FIG. 11d, of the composite signal C+D in FIG. 11e, of the thread jump signal in FIG. 11f and of the output signal III in FIG. 11g.

Figure 11A:
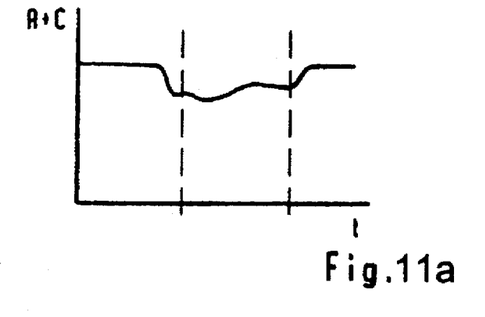
Figure 11B:
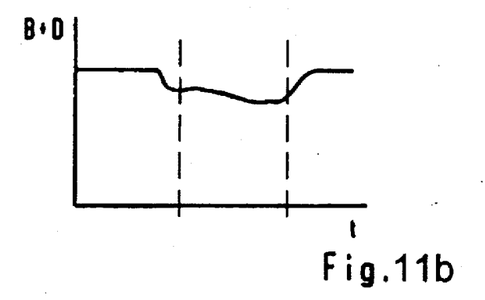
Figure 11C:
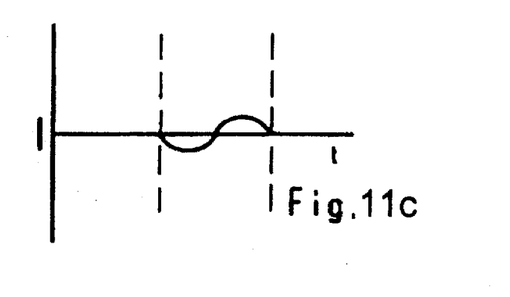
Figure 11D:
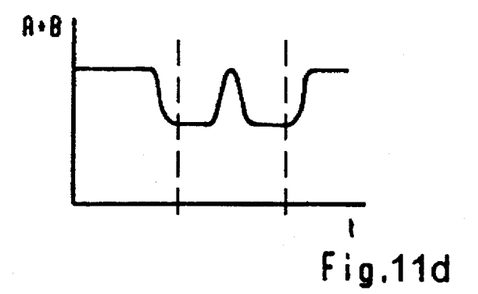
Figure 11E:
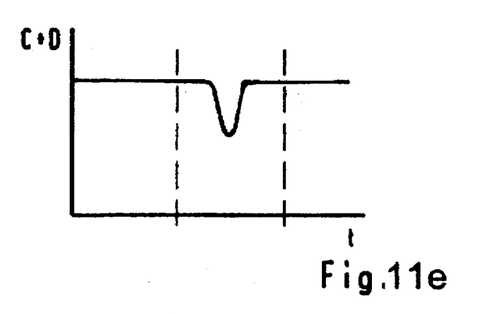
Figure 11F:
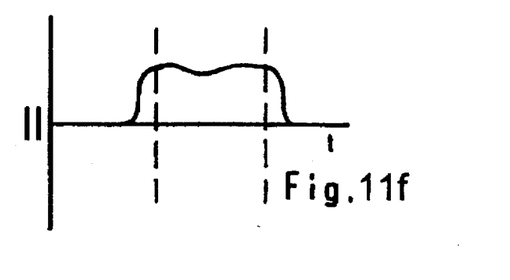
Figure 11G:
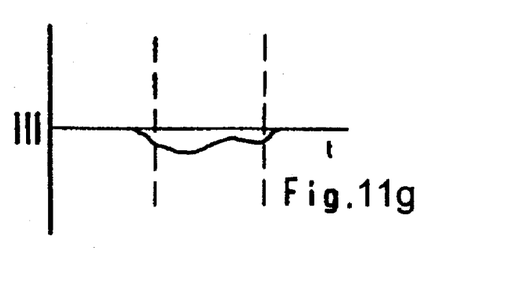

Here too, it can be seen in FIG. 11g that the time sequence of output signal III does not exhibit positive values and therefore when compared to the lower threshold value 117 no signal IV is relayed, although as shown in FIG. 11c the real thread jump will emit a lint signal I similar to the one emitted by a small or middle-sized lint.

Figure 12:
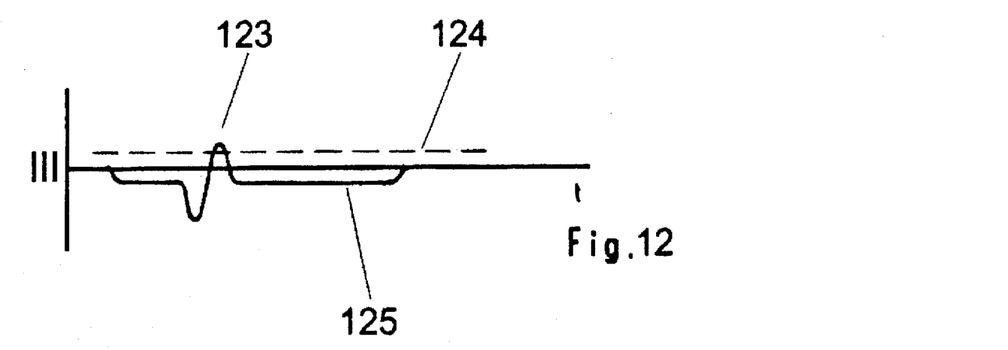
FIG. 12 shows a waveform when small lints and a thread jump occur.

FIGS. 9g, 10g and 11g make clear that the time sequence during which a signal is formed is significantly longer when thread jumps are present than when lints are present. FIGS. 9a through 11g also make it clear that when a thread jump and a lint are present simultaneously, smaller lints can also be detected easily by means of the circuit provided. The time sequence of a concurrent presence of a thread jump and a lint is depicted in FIG. 12. The sequence of the signal is referred to in the illustration as 125. By appropriate adjustment of the lower threshold value to a level as depicted in FIG. 12 by broken line 124, it can be seen that the upper amplitude 123, which is derived from the lint, exceeds the threshold value and in so doing causes an output signal IV so that the lint is clearly recognizable. It is surprising that the measurement and precision can be so significantly improved when the number of photodetectors is increased and when they are properly positioned.

Figure 13:
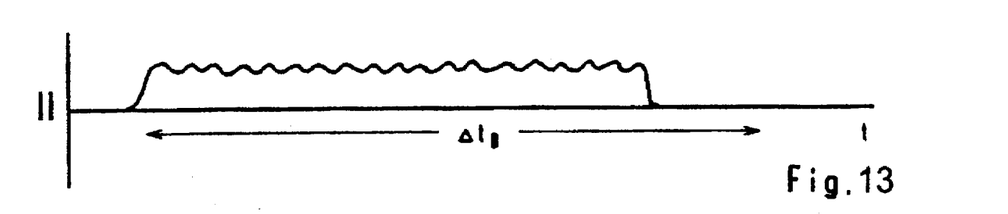
FIG. 13 shows the waveform when a thread break occurs.
Figure 14:
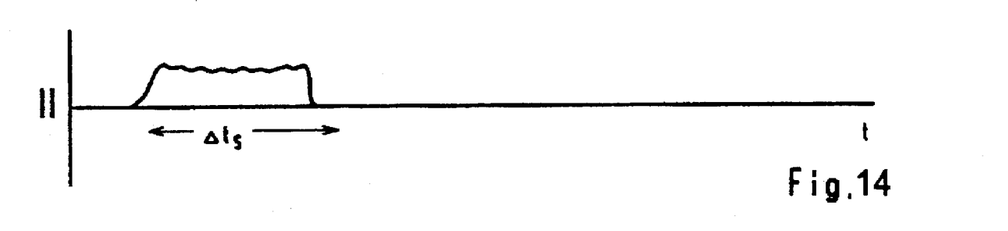
FIG. 14 shows the waveform when a thread jump occurs.

Surprisingly, it also became evident during the execution of the process of the invention that the process of the invention is also perfectly suited for the detection of thread breaks when at least four photodetectors are employed. It has been found that in case of a thread break a signal II comparable to the presence of a thread jump is obtained, although this signal is significantly longer in case of a thread break than the signal detected for a thread jump. FIG. 13 depicts the time sequence of the thread jump signal relating to the case of a thread break, whereas FIG. 14 illustrates the time sequence of a thread jump signal in the case of a thread jump. Therefore, a thread break can be detected easily by electronic means by comparing the duration with a maximum permissible time limit. As long as the duration is under this maximum permissible time limit the signal is considered as a thread jump, whereas in case of a signal exceeding the maximum permissible time limit a thread break is undoubtedly present. A typical maximum permissible time limit for the signal to be present for a thread jump is clearly under 40 ms (milliseconds), whereas in case of thread breaks time values of 40 ms or more are detected.

Figure 15:
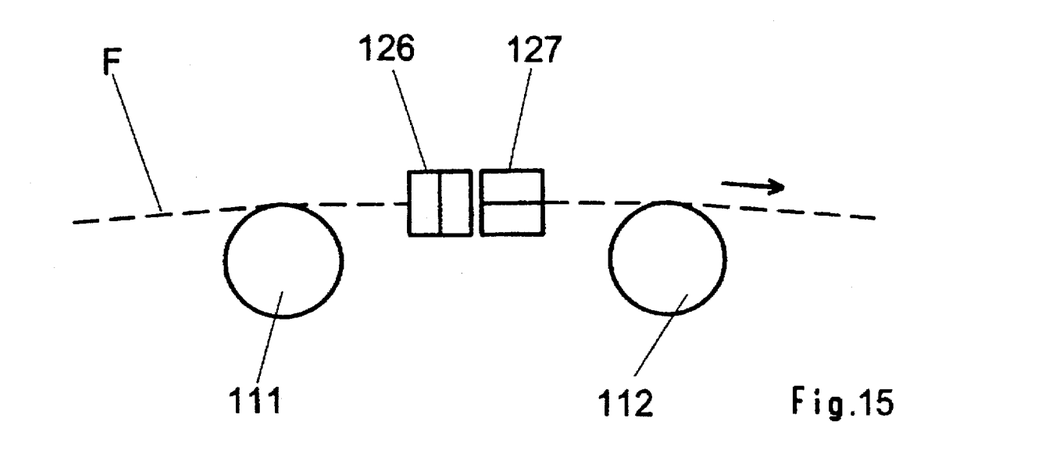
FIG. 15 shows another arrangement for the execution of the process of the invention.

FIG. 15 depicts a further embodiment of the process of the invention. The yarn sheet F is again guided via thread guide rods 111 and 112. Two double photodetector units are positioned between the two thread guide rods 111 and 112, whereby double photodetector unit 126 is laid out in such a manner that the two photocells are arranged in series in the direction of travel and the yarn sheet moves past both photocells. The photodetector unit 127 is so arranged that the two photocells are arranged one above the other and the yarn sheet runs between them. Based on the above explanations concerning a four-quadrant photodetector, it becomes clear that even the simplified embodiment according to FIG. 2 as well as according to FIG. 15 delivers satisfactory results, but that the use of four-quadrant photodetectors allows a more precise monitoring of the yarn sheet. It also becomes evident in using multisegment photodetectors, however, that the precision increases as more photocells are employed.

As a result of the above explanations it becomes evident that, by means of multisegment photodetectors with help from electronic circuitry, interference signals caused by thread jumps are effectively suppressed. Therefore the lower switching threshold, by which the smallest lint which is detectable is evaluated, can be adjusted significantly lower. By means of the process of the invention a higher sensitivity to lint detection is obtained without having miscounts and/or faulty stops increased to a marked degree. The detection of smaller lints facilitates the production of yarns of higher quality. Avoiding faulty stops maintains production stoppage at a low level and increases productivity. If only relatively large lints are to be eliminated by cessations of machine operation (settable by the upper threshold value), the process of the invention permits an accurate statement on the number of smaller lints. At the same time, a statement concerning the quality of the yarn sheet is possible.

While the invention has been described with preferred embodiments, it is to be understood that variations and modifications are to be considered within the purview and the scope of the claims appended hereto.

What is claimed is:

1. A process for monitoring a moving yarn sheet comprising guiding said yarn sheet via thread guide rods before and after a monitoring site, emitting a single light beam perpendicularly to the direction of travel of said yarn sheet and parallel to the yarn sheet plane to photodetectors, evaluating and recording the signals of said photodetectors by an electronic analyzer, detecting the intensity of said single light beam by at least two of said photodetectors arranged in series in the direction of travel of said yarn sheet, carrying out the evaluation by said electronic analyzer such that a recording only takes place when the shadow projected upon one or more photodetectors which are sequentially arranged in the direction of travel of said yarn sheet is detected as having a time delay corresponding to the running speed of said yarn sheet, widening said light beam to a maximal 30 mm before striking said yarn sheet and focusing the width of said light beam beyond said yarn sheet such that it illuminates all photodetectors assigned to it.

2. The process in accordance with claim 1, wherein the said light beam is widened up to a maximal 10 mm and then sent through the yarn sheet and that said light beam is focused beyond said yarn sheet such that it covers at least the entire surface area of all photodetectors assigned to it.

3. The process according to claim 1, wherein two photodetectors are employed, said two photodectors being contained in one double photodetector.

4. The process according to claim 1, wherein two photodetectors in series are employed, the amplified signals from each of said two photodetectors in series struck by a single light beam are directed to a differential amplifier and in that the electronic analyzer only transmits a signal for recording when the differential signal exceeds a predetermined level.

5. A process for monitoring a moving yarn sheet, wherein the process is, according to claim 1, repeated in the direction of travel of said yarn sheet.

6. A process for monitoring a moving yarn sheet comprising guiding said yarn sheet by means of thread guide rods before and after a monitoring site, emitting at least one light beam perpendicularly to the direction of travel of said yarn sheet and parallel to the yarn sheet plane to photodetectors evaluating and recording the signals of said photodetectors by means of an electronic analyzer, employing one or more light beams and at least four photodetectors for monitoring, of which at least two are positioned in series in the direction of travel of the yarn sheet and at least two are positioned one above the other such that at least one photodetector is situated below and one photodetector is situated above the yarn sheet plane.

7. The process according to claim 6, wherein 50% of all photodetectors are arranged above the yarn sheet plane and 50% of all photodetectors are positioned below it.

8. The process according to claim 6, wherein each upper photodetector is arranged adjacent to one lower photodetector.

9. A process according to claim 8, wherein the electronic analyzer detects a lint signal I, formed by adding up the signals emitted by the photodetectors arranged one above another and by subtracting the sums detected by two photodetector pairs in series and determines a thread jump signal II, which is formed by adding up the signals emitted by two photodetectors arranged in series and by the difference of the sums detected by two photodetector pairs arranged one above the other, and in that a lint is recorded when the attenuated thread jump signal II is subtracted from lint signal I and the difference exceeds a predetermined lower threshold value.

10. The process according to claim 9, wherein said electronic analyzer emits a stop signal VI if the lint signal I exceeds a predetermined upper threshold value and at the same time a lint has been recorded.

11. The process according to claim 9, wherein the electronic analyzer determines the size of the lint by the strength of the lint signal (I) when a lint is recorded.

12. The process according to claim 6, wherein photodetectors which are arranged in series are adjacent.

13. The process according to claim 6, wherein all photodetectors are illuminated by a single light beam.

14. The process according to claim 13, wherein the light beam is widened before striking the yarn sheet.

15. The process according to claim 14, wherein the light beam is widened up to a maximal 30 mm and that the width of the light beam is focused beyond the yarn sheet such that it illuminates all photodetectors assigned to it.

16. The process according to claim 15, wherein the light beam is sent through the yarn sheet with a width not exceeding 10 mm and is focused beyond the yarn sheet to a width not exceeding 6 mm.

17. The process according to claim 6, wherein the process is carried out using double photodetectors.

18. The process according to claim 6, wherein the process is carried out using a four-quadrant photodetector.

19. The process according to claim 6, wherein the process is carried out using a multisegment photodetector.

20. An apparatus for monitoring a moving yarn sheet according to claim 6 with at least one light source and photodetectors, wherein the apparatus possesses at least four photodetectors, of which at least two photodetectors are positioned in series in the direction of travel of the yarn sheet and at least two photodetectors are arranged one above the other.

21. The apparatus according to claim 20, wherein all photodetectors are arranged such that respective pairs are formed one above the other and all pairs are arranged in series.

22. The apparatus according to claim 20, wherein 50% of all photodetectors are positioned above a yarn sheet plane and 50% of all photodetectors are positioned below it.

23. An apparatus according to claim 20, wherein the light beam consists of collimated light.

24. An apparatus according to claim 20, wherein the light beam is a laser beam.

* * * * *